United States Patent
Mittal et al.

(10) Patent No.: US 12,215,101 B2
(45) Date of Patent: *Feb. 4, 2025

(54) PRO DRUGS OF PDE10 COMPOUNDS

(71) Applicant: Merck Sharp & Dohme LLC, Rahway, NJ (US)

(72) Inventors: Sachin Mittal, Bridgewater, NJ (US); Jason W. Skudlarek, Audubon, PA (US); Izzat T. Raheem, Doylestown, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,309

(22) Filed: Dec. 13, 2023

(65) Prior Publication Data

US 2024/0158388 A1 May 16, 2024

Related U.S. Application Data

(63) Continuation of application No. 17/695,125, filed on Mar. 15, 2022, now Pat. No. 11,919,894.

(60) Provisional application No. 63/162,333, filed on Mar. 17, 2021.

(51) Int. Cl.
*C07D 417/14* (2006.01)

(52) U.S. Cl.
CPC .................. *C07D 417/14* (2013.01)

(58) Field of Classification Search
CPC .................................................. C07D 417/14
USPC ......................................................... 514/269
See application file for complete search history.

(56) References Cited

U.S. PATENT DOCUMENTS

| | | | |
|---|---|---|---|
| 8,106,209 B2 | 1/2012 | Liu | |
| 9,062,059 B2 | 6/2015 | Cox et al. | |
| 11,919,894 B2 * | 3/2024 | Mittal | C07D 417/14 |
| 2003/0119814 A1 | 6/2003 | Guarino | |

FOREIGN PATENT DOCUMENTS

| | | |
|---|---|---|
| WO | 2009149436 A1 | 12/2009 |
| WO | 2013028590 A1 | 2/2013 |

OTHER PUBLICATIONS

Aitipamula, S., et al., "Polymorphs, Salts, and Cocrystals: What's In A Name", Crystal Growth and Design, 2012, pp. 2147-2152, vol. 12.

Becker et al., Phosphodiesterase Inhibitors—Are They Potential Neuroleptic Drugs?, Behavioural Brain research, 2008, pp. 155-160, 186.
Fujishige et al., Cloning and Characterization of a Novel Human Phosphodiesterase That Hydrolyzes Both CAMPand cGMP (PDE10A), J. of Biological Chemistry, Jun. 25, 1999, pp. 18438-18445, 274.
Huang et al., A Fluroescence Polarization Assay for Cyclic Nucleotide Phosphodiesterases, J. of Biomolecular Screening, 2002, pp. 215-222, 7.
Kehler, The Potential Therapeutic Use of Phosphodiesterase 10 Inhibitors, Expert Opinion, 2007, pp. 147-158, 17.
Lieberman et al., Effectiveness of Antipsychotic Drugs in Patients with Chronic Schizophrenia, New England J. of Medicine, Sep. 22, 2005, pp. 1209-1223, 353, US.
Loughney et al., Isolation and Characterization of PDE10A, a Novel Human 3', 5'-Cyclic Nucleotide Phosphodiesterase, Gene, 1999, pp. 109-117, 234.
Mosser et al., Automation of In Vitro Dose-Inhibition Assays Utlizing the Tecan Genesis and an Integratd Software Package to Support the Drug Discovery Process, JALA, 2003, pp. 54-63, 8, Sage Publications.
Rautio, J., et al, "Prodrugs: Design And Clinical Applications", Prodrugs of Alcohols and Phenols, 2008, pp. 255-270, vol. 7, No. 3, US.
Schmidt et al., Pre-clincal Characterization of Selective PHosphodiesterease 10A Inhibitors: A New Therapeutic Approach to the Treatment of Schizophrenia, J. of Pharmacology and Experimental Thereapeutics, 2008, pp. 690-690, 325.
Siuciak et al., Inhibiton of the Striatum-Enriched Phosphodiesterease PDE10A: A novel Approach to the Treament of Psychosis, Neuropharmacology, 2006, pp. 386-396, 51.
Soderling et al., Isolation and Characterization of a Dual-Substrate Phosphodiesterase Gene Family: PDE10A, Proc. Natl. Acad. Sci. USA, Jun. 1999, pp. 7071-7076, 96.
Threlfell et al., Inhibition of Phosphodiesterase 10A Increases the Responsiveness of Striatal Projection Neurons to the Cortical Stimulation, J. of Pharmacology and Experimental Therapeutics, J. of Pharmacology and Experimental Therapeutics, 2009, pp. 785-795, 328.
Guarino, Victor R. et al., Sulfenamides as prodrugs of NH-acidic compounds: A new prodrug option for the amide bond, Bioorg. Med. Chem. Lett., 17, 4910-4913, 2007.
Simplicio, A. L. et al., Prodrugs for Amines, Molecules, vol. 13, p. 519-547, 2008.

* cited by examiner

*Primary Examiner* — Kahsay Habte
(74) *Attorney, Agent, or Firm* — Sylvia A. Ayler; Catherine D. Fitch

(57) ABSTRACT

The present invention is directed to pro drugs of 2-methyl-N-((5-methyl-1,3,4-thiadiazol-2-yl)methyl)-6-(((1S,2S)-2-(5-methylpyridin-2-yl)cyclopropyl)methoxy)pyrimidin-4-amine which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

3 Claims, No Drawings

PRO DRUGS OF PDE10 COMPOUNDS

CROSS-REFERENCE TO RELATED APPLICATIONS

This application claims the benefit of priority to U.S. Provisional Application No. 63/162,333, filed Mar. 17, 2021, the disclosure of which is incorporated herein by its entirety.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olartzapine) antipsychotics, have been less than acceptable and result in an extremely high rate of noncompliance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., *N. Engl. J. Med.* (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3', 5'-cyclic nucleotide specific phosphodiesterases (PDEs). The identification of PDE10 was reported by three groups independently and was distinguished from other PDEs on the basis of its amino acid sequence, functional properties, and tissue distribution (Fujishige et al., *J. Biol. Chem.* (1999) 274:18438-18445; Loughney et al., *Gene* (1999) 234: 109-117; Soderling et al., *PNAS.* USA (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PK.A phosphorylation site that upon activation, i.e. PK.A phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., *Expert Opin. Ther. Patents* (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions.

Inhibition of PDE10 is believed to be useful in the treatment of schizophrenia and a wide variety of conditions or disorders that would benefit from increasing levels of cAMP and/or cGMP within neurons, including a variety neurological, psychotic, anxiety and/or movement disorders. U.S. Pat. No. 9,062,059 (incorporated herein in its entirety) discloses PDE10 inhibitors including 2-methyl-N-((5-methyl-1,3,4-thiadiazol-2-yl)methyl)-6-(((1S,2S)-2-(5-methylpyridin-2-yl)cyclopropyl)methoxy)pyrimidin-4-amine. as therapeutics for neurological and psychiatric disorders.

SUMMARY OF THE INVENTION

The present invention is directed to certain derivatives of cyclopyrimidine amine derivatives. The compounds of Formula I are believed to be prodrugs which can be metabolized in vivo to 2-methyl-N-((5-methyl-1,3,4-thiadiazol-2-yl)methyl)-6-(((1S,2S)-2-(5-methylpyridin-2-yl)cyclopropyl)methoxy)pyrimidin-4-amine (Compound A) and inhibit PDE10. Compound A inhibits the polymerase function of PDE10, and more particularly inhibit the dopaminergic D2 receptor activity associated with cAMP of PDE10. Thus, the compounds of Formula I, are useful, for example in the in the inhibition of phosphodiesterase 10 (PDE10), for the treatment of central nervous system disorders associated with phosphodiesterase 10 (PDE10), to facilitate administration of Compound A, and to treat schizophrenia, as well as a variety of neurological, psychotic, anxiety and/or movement disorders.

DETAILED DESCRIPTION OF THE INVENTION

The present invention is directed to compounds of structural Formula I:

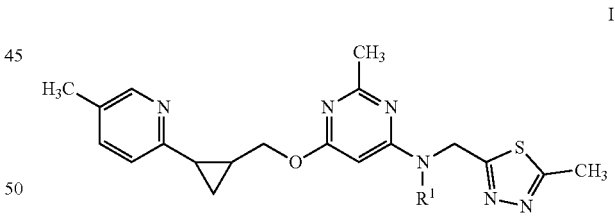

or pharmaceutically acceptable salt thereof, wherein:
$R^1$ is selected from the group consisting of
1) —C(O)OCH$_2$OC(O)R$^2$;
2) —C(O)OC$_{1-16}$ alkyl, said alkyl optionally substituted with 1 to 3 groups of R$^a$;
3) —C(O)—C$_{6-10}$ aryl, C(O)—C$_{6-10}$heteroaryl, —C(O)—C$_{1-6}$ alkyl, —C(O)—C$_{3-6}$ cycloalkyl said aryl, heteroaryl, alkyl and cycloalkyl optionally substituted with 1 to 3 groups of R$^a$;
4) —S—C$_{6-10}$ aryl, —S—C$_{4-10}$heteroaryl, —S—C$_{1-6}$ alkyl, —S—C$_{3-6}$ cycloalkyl said aryl, heteroaryl, alkyl and cycloalkyl optionally substituted with 1 to 3 groups of R$^a$; and
5) —C(O)OCH$_2$dioxolyl, optionally substituted with 1 to 2 groups of R$^a$;

R$^2$ is selected from the group consisting of C$_{1-6}$ alkyl, C$_{6-10}$ aryl, C$_{4-10}$ heteroaryl, and C$_{3-6}$ cycloalkyl; said alkyl, aryl heteroaryl, and cycloalkyl optionally substituted with 1 to 3 groups of R$^a$;

R$^a$ is independently selected from the group consisting of C$_{1-6}$ alkyl, OC$_{1-6}$ alkyl, oxo, and halogen;

n is 1, 2, 3, or 4.

Another embodiment of this invention is realized when R$^1$ is —C(O)OCH$_2$OC(O)R$^2$. A subembodiment of this aspect of the invention is realized when R$^2$ is C$_{1-6}$ alkyl, said alkyl unsubstituted or substituted with 1 to 3 groups of R$^a$. Another subembodiment of this aspect of the invention is realized when R$^2$ is C$_{6-10}$ aryl, said aryl unsubstituted or substituted with 1 to 3 groups of R$^a$. A further subembodiment of this aspect of the invention is realized when the aryl is unsubstituted or substituted phenyl or naphthyl. Still another subembodiment of this aspect of the invention is realized when R$^2$ is C$_{6-10}$ heteroaryl, said heteroaryl unsubstituted or substituted with 1 to 3 groups of R$^a$. A further subembodiment of this aspect of the invention is realized when the heteroaryl is unsubstituted or substituted pyridyl or pyrimidinyl. Yet another subembodiment of this aspect of the invention is realized when R$^2$ is C$_{3-6}$ cycloalkyl; said cycloalkyl unsubstituted or substituted with 1 to 3 groups of R$^a$. A further subembodiment of this aspect of the invention is realized when the cycloalkyl is unsubstituted or substituted cyclobutyl, cyclopentyl or cyclohexyl.

Another embodiment of this invention is realized when R$^2$ is selected from the group consisting of C$_{1-6}$ alkyl, phenyl, pyridyl and cyclohexyl, said groups unsubstituted or substituted with 1 to 3 groups of R$^a$.

Another embodiment of this invention is realized when R$^1$ is C(O)OC$_{1-6}$ alkyl, said alkyl optionally substituted with 1 to 3 groups of R$^a$.

An embodiment of this invention is realized when R$^1$ is —C(O)OCH$_2$dioxolyl, said dioxolyl optionally substituted with 1 to 3 groups of R$^a$. A subembodiment of this aspect of the invention is realized when the dioxolyl is unsubstituted or substituted with 1 to 2 groups independently selected from R$^a$. Another subembodiment of this aspect of the invention is realized when the dioxolyl is unsubstituted. Another subembodiment of this aspect of the invention is realized when the dioxolyl is independently substituted with 1 to 2 groups of C$_{1-6}$ alkyl or oxo. Another subembodiment of this aspect of the invention is realized when the dioxolyl is independently substituted with 1 to 2 groups of C$_{1-6}$ alkyl and oxo. Yet another subembodiment of this aspect of the invention is realized when dioxolyl is substituted with CH$_3$ and oxo. Still another subembodiment of this aspect of the invention is realized when R$^1$ is represented by (i):

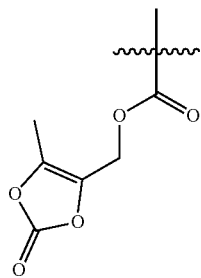

(i)

wherein the squiggly line represents the point of attachment.

Another embodiment of this invention is realized when R$^1$ is —S—C$_{6-10}$ aryl, said aryl optionally substituted with 1 to 3 groups of R$^a$. A subembodiment of this aspect of the invention is realized when the aryl is phenyl or naphthyl, said phenyl and naphthyl unsubstituted or substituted with 1 to 3 groups of R$^a$. Another subembodiment of this aspect of the invention is realized when R$^1$ is phenyl, unsubstituted or substituted with 1 to 3 groups of R$^a$. Another subembodiment of this aspect of the invention is realized when R$^1$ is unsubstituted phenyl. Another subembodiment of this aspect of the invention is realized when R$^1$ is substituted phenyl. A subembodiment of this aspect of the invention is realized when the aryl is unsubstituted or substituted naphthyl.

Another embodiment of this invention is realized when R$^1$ is —S—C$_{4-10}$heteroaryl, said heteroaryl optionally substituted with 1 to 3 groups of R$^a$. A subembodiment of this aspect of the invention is realized when the heteroaryl is selected from pyridyl, pyrimidinyl, pyrrolyl, pyrazolyl, oxazolyl and the like, said pyridyl, pyrimidinyl, pyrrolyl, pyrazolyl, and oxazolyl unsubstituted or substituted with 1 to 3 groups of R$^a$. Another subembodiment of this aspect of the invention is realized when R$^1$ is pyridyl, unsubstituted or substituted with 1 to 3 groups of R$^a$. Another subembodiment of this aspect of the invention is realized when R$^1$ is unsubstituted or substituted pyrimidinyl. Another subembodiment of this aspect of the invention is realized when R$^1$ is unsubstituted or substituted pyrrolyl. Another subembodiment of this aspect of the invention is realized when R$^1$ is unsubstituted or substituted pyrazolyl. Another subembodiment of this aspect of the invention is realized when R$^1$ is unsubstituted or substituted oxazolyl.

Another embodiment of this invention is realized when R$^1$ is —S—C$_{1-6}$alkyl, said alkyl optionally substituted with 1 to 3 groups of R$^a$. Another embodiment of this invention is realized when R$^1$ is —S—C$_{3-6}$ cycloalkyl, said cycloalkyl optionally substituted with 1 to 3 groups of R$^a$. A subembodiment of this aspect of the invention is realized when the cycloalkyl is selected from the group consisting of cyclopropyl, cyclobutyl, cyclopentyl, and cyclohexyl.

Another embodiment of this invention is realized when R$^1$ is —C(O)—C$_{6-10}$ aryl, said aryl optionally substituted with 1 to 3 groups of R$^a$. A subembodiment of this aspect of the invention is realized when the aryl is phenyl or naphthyl, said phenyl and naphthyl unsubstituted or substituted with 1 to 3 groups of R$^a$. Another subembodiment of this aspect of the invention is realized when R$^1$ is phenyl, unsubstituted or substituted with 1 to 3 groups of R$^a$. Another subembodiment of this aspect of the invention is realized when R$^1$ is unsubstituted phenyl. Another subembodiment of this aspect of the invention is realized when R$^1$ is substituted phenyl. A subembodiment of this aspect of the invention is realized when the aryl is unsubstituted or substituted naphthyl.

Another embodiment of this invention is realized when R$^1$ is —C(O)—C$_{4-10}$heteroaryl, said heteroaryl optionally substituted with 1 to 3 groups of R$^a$. A subembodiment of this aspect of the invention is realized when the heteroaryl is selected from pyridyl, pyrimidinyl, pyrrolyl, pyrazolyl, oxazolyl and the like, said pyridyl, pyrimidinyl, pyrrolyl, pyrazolyl, and oxazolyl unsubstituted or substituted with 1 to 3 groups of R$^a$. Another subembodiment of this aspect of the invention is realized when R$^1$ is pyridyl, unsubstituted or substituted with 1 to 3 groups of R$^a$. Another subembodiment of this aspect of the invention is realized when R$^1$ is unsubstituted or substituted pyrimidinyl. Another subembodiment of this aspect of the invention is realized when R$^1$ is unsubstituted or substituted pyrrolyl. Another subembodiment of this aspect of the invention is realized when R$^1$ is unsubstituted or substituted pyrazolyl. Another subembodiment of this aspect of the invention is realized when $R^1$ is unsubstituted or substituted oxazolyl.

Another embodiment of this invention is realized when $R^1$ is —C(O)—$C_{1-6}$alkyl, said alkyl optionally substituted with 1 to 3 groups of R. Another embodiment of this invention is realized when $R^1$ is —C(O)—$C_{3-6}$ cycloalkyl, said cycloalkyl optionally substituted with 1 to 3 groups of $R^a$. A subembodiment of this aspect of the invention is realized when the cycloalkyl is selected from the group consisting of cyclopropyl, cyclobutyl, cyclopentyl, and cyclohexyl.

The present invention includes the pharmaceutically acceptable salts of the compounds defined in all structural Formulas, embodiments and classes thereof described herein. Reference to the compounds of Formula I herein encompasses the compounds of Formulas I and all embodiments and classes thereof. Reference to the compounds of this invention as those of a specific formula or embodiment, e.g., Formula I, or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise.

The present invention includes each of the Examples described herein, and pharmaceutically acceptable salts thereof. The invention also encompasses pharmaceutical compositions comprising an effective amount of a compound of the invention or a pharmaceutically acceptable salt thereof, and a pharmaceutically acceptable carrier.

Unless expressly stated to the contrary, substitution by a named substituent is permitted on any atom in a chain or ring provided such substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

Exemplifying the invention are the specific compounds disclosed in the Examples and herein. The subject compounds are useful in a method of treating a neurological or psychiatric disorder associated with PDE10 dysfunction in a patient such as a mammal in need of such inhibition comprising the administration of an effective amount of the compound. In addition to primates, especially humans, a variety of other mammals can be treated according to the method of the present invention, including those research animals and companion animals such as mice, rats, primates, monkeys, chimpanzees, great apes, dogs, and house cats. The subject compounds are useful in a method of inhibiting PDE10 activity in a patient such as a mammal in need of such inhibition comprising the administration of an effective amount of the compound. The subject compounds are also useful for treating a neurological or psychiatric disorder associated with striatal hypofunction or basal ganglia dysfunction in a mammalian patient in need thereof.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basai ganglia dysfunction in a mammalian patient in need thereof.

As used herein, "alkyl" refers to both branched- and straight-chain saturated aliphatic hydrocarbon groups having the specified number of carbon atoms in a specified range. For example the term "$C_{1-10}$ alkyl" means linear or branched chain alkyl groups, including all possible isomers, having 1, 2, 3, 4, 5, 7, 8, 9 or 10 carbon atoms, and includes each of the decyl, nonyl, octyl, heptyl, hexyl and pentyl isomers as well as n-, iso-, sec- and tert-butyl (butyl, s-butyl, i-butyl, t-butyl; Bu=butyl, collectively "—$C_4$alkyl"), n- and iso-propyl (propyl, i-propyl, Pr=propyl, collectively "—$C_3$alkyl"), ethyl (Et) and methyl (Me). "$C_{1-4}$alkyl" has 1, 2, 3 or 4 carbon atoms, and includes each of n-, iso-, sec- and tert-butyl, n- and i-propyl, ethyl and methyl.

"Cycloalkyl" refers to a cyclized alkyl ring having the indicated number of carbon atoms in a specified range. Thus, for example, "$C_{3-8}$ cycloalkyl" encompasses each of cyclopropyl, cyclobutyl, cyclopentyl, cyclohexyl, cycloheptyl and cyclooctyl. "$C_{3-6}$cycloalkyl" encompasses each of cyclopropyl, cyclobutyl, cyclopentyl and cyclohexyl. When cycloalkyl is a substituent on an alkyl group in a compound of Formula I, the cycloalkyl substituent can be bonded to any available carbon in the alkyl group. The following are illustrations of —$C_{3-6}$cycloalkyl substituents wherein the substituent is cyclopropyl in bold:

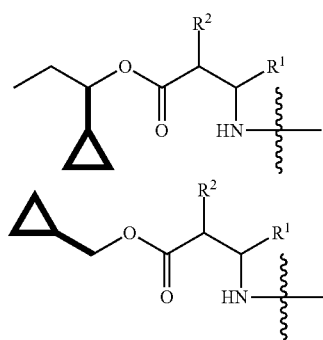

"Aryl" refers to (i) phenyl, (ii) 9- or 10-membered bicyclic, fused carbocylic ring systems in which at least one ring is aromatic, and (iii) 11- to 14-membered tricyclic, fused carbocyclic ring systems in which at least one ring is aromatic. Suitable aryls include, for example, substituted and unsubstituted phenyl and substituted and unsubstituted naphthyl. An aryl of particular interest is unsubstituted or substituted phenyl.

"Heteroaryl" refers to (i) a 5- or 6-membered heteroaromatic ring containing from 1 to 4 heteroatoms independently selected from N, O and S, wherein each N is optionally in the form of an oxide, and (ii) a 9- or 10-membered bicyclic fused ring system, wherein the fused ring system of (ii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or $S(O)_2$. Suitable 5- and 6-membered heteroaromatic rings include, for example, pyridyl, 3-fluoropyridyl, 4-fluoropyridyl, 3-methoxypyridyl, 4-methoxypyridyl, pyrrolyl, pyrazinyl, pyrimidinyl, pyridazinyl, triazinyl, thienyl, furanyl, imidazolyl, pyrazolyl, triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, isoindolyl, benzopiperidinyl, benzofuranyl, imidazo[1,2-a]pyridinyl, benzotriazolyl, indazolyl, indolinyl, and isoindolinyl. A class of heteroaryls includes unsubstituted or substituted pyridyl or pyrimidyl, and particularly unsubstituted or substituted pyridyl.

The term "heterocyclic or "heterocyclyl" refers to (i) a saturated 4- to 7-membered cyclized ring and (ii) an unsaturated, non-aromatic 4 to 7-membered cyclized ring comprised of carbon atoms and 1-4 heteroatoms independently selected from O, N and S. Heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated, non-aromatic heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond). A class of heterocyclic rings are 4 to 6-membered saturated monocyclic rings comprised of carbon atoms and 1 or 2 heteroatoms, wherein the heteroatoms are selected from N, O and S. Examples of 4 to 6 membered heterocyclic rings include but are not limited to, azetidinyl, pyrrolidinyl, piperidinyl, piperazinyl, morpholinyl, thiomorpholinyl, tetrahydrofuranyl, tetrahydropyranyl and tetrahydrothiopyranyl, and a sub-class thereof is piperidinyl, pyrrolidinyl, tetrahydrofuranyl or tetrahydropyranyl.

As would be recognized by one of ordinary skill in the art, certain compounds of the present invention may be able to exist as tautomers. All tautomeric forms of these compounds, whether isolated individually or in mixtures, are within the scope of the present invention. For example, in instances where an —OH substituent is permitted on a heteroaromatic ring and keto-enol tautomerism is possible, it is understood that the substituent might in fact be present, in whole or in part, in the oxo (=O) form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments. For example, certain moieties as defined in Formula I may be unsubstituted or substituted, and the latter is intended to encompass substitution patterns (i.e., number and kind of substituents) that are chemically possible for the moiety and that result in a stable compound.

A compound of Formula I may have multiple chiral centers (also referred to as asymmetric or stereogenic centers. This invention encompasses compounds having either the (R) or (S) stereo-configuration at a phosphorus assymetric center and at any additional assymetric centers that may be present in a compound of Formula I, as well as stereoisomeric mixtures thereof.

This invention includes individual diastereomers, particularly epimers, i.e., compounds having the same chemical formula but which differ in the spatial arrangement around a single atom. This invention also includes mixtures of diastereomers, particularly mixtures of epimers, in all ratios. Embodiments of this invention also include a mixture of epimers enriched with 51% or more of one of the epimers, including for example 60% or more, 70% or more, 80% or more, or 90% or more of one epimer. A single epimer is preferred. An individual or single epimer refers to an epimer obtained by chiral synthesis and/or using generally known separation and purification techniques, and which may be 100% of one epimer or may contain small amounts (e.g., 10% or less) of the opposite epimer. Thus, individual diastereomers are a subject of the invention in pure form, both as levorotatory and as dextrorotatory antipodes, in the form of racemates and in the form of mixtures of the two diastereomers in all ratios. In the case of a cis/trans isomerism the invention includes both the cis form and the trans form as well as mixtures of these forms in all ratios.

The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

The compounds can be administered in the form of pharmaceutically acceptable salts. The term "pharmaceutically acceptable salt" refers to a salt which is not biologically or otherwise undesirable (e.g., is neither toxic nor otherwise deleterious to the recipient thereof). Since the compounds of Formula I contain by definition at least one basic group, the invention includes the corresponding pharmaceutically acceptable salts. When the compounds of Formula I contain one or more acidic groups, the invention also includes the corresponding pharmaceutically acceptable salts. Thus, the compounds of Formula I that contain acidic groups (e.g., —COOH) can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I, which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the compounds of of this invention are likewise encompassed within the scope of the compounds defined by Formula I and the pharmaceutically acceptable salts thereof, along with un-solvated and anhydrous forms of such compounds.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, where such forms are possible unless specified otherwise.

The instant invention encompasses any composition comprised of a compound of Formula I or a compound that is a salt thereof, including for example but not limited to, a composition comprised of said compound associated together with one or more additional molecular and/or ionic component(s) which may be referred to as a "co-crystal." The term "co-crystal" as used herein refers to a solid phase (which may or may not be crystalline) wherein two or more different molecular and/or ionic components (generally in a stoichiometric ratio) are held together by non-ionic interactions including but not limited to hydrogen-bonding, dipole-dipole interactions, dipole-quadrupole interactions or dispersion forces (van der Waals). There is no proton transfer between the dissimilar components and the solid phase is neither a simple salt nor a solvate. A discussion of co-crystals can be found, e.g., in S. Aitipamula et al., *Crystal Growth and Design,* 2012, 12 (5), pp. 2147-2152.

More specifically with reference to this invention, a co-crystal is comprised of a compound of Formula I or a pharmaceutically acceptable salt thereof, and one or more non-pharmaceutically active component(s) which is not biologically or otherwise undesirable (e.g., is neither toxic nor otherwise deleterious to the recipient thereof). Co-crystals can be obtained from a compound of Formula I, or a pharmaceutically acceptable salt thereof, by customary methods known in the chemical arts. For example, co-crystals comprised of a compound of this invention could be prepared by adding an acid or a neutral molecule at the desired stoichiometry to the compound, adding an appropriate solvent to achieve dissolution and, for example, precipitating, lyophilizing or concentrating the solution to obtain the solid composition. The co-crystal can be, but is not limited to, an embodiment wherein the composition is comprised of a neutral compound (i.e. not a salt form) of Formula I and one or more non-pharmaceutically active component(s); and in a further embodiment, the co-crystal composition is crystalline. Crystalline compositions may be prepared, for example, by adding an acid or a neutral molecule at the desired stoichiometry to the compound of Formula I, adding an appropriate solvent and heating to achieve complete dissolution, and then allowing the solution to cool and the crystals to grow. The present invention also includes all co-crystals of the compounds of this invention which, owing to low physiological compatibility, are not directly suitable for use in pharmaceuticals but which can be used, for example, as intermediates for chemical reactions or for the preparation of pharmaceutically acceptable co-crystals or salts.

Accordingly, the compounds of Formula I, embodiments thereof and specific compounds described and claimed herein encompass all possible pharmaceutically acceptable salts, stereoisomers, tautomers, physical forms (e.g., amorphous and crystalline forms), co-crystal compositions, solvate and hydrate forms and any combination of the foregoing forms where such forms are possible.

The compounds of Formula I described herein are prodrugs. A discussion of prodrugs is provided in (a) Stella, V. J.; Borchardt, R. T.; Hageman, M. J.; Oliyai, R.; Maag, H. et al. *Prodrugs: Challenges and Rewards Part 1 and Part 2*; Springer, p. 726: New York, NY, USA, 2007, (b) Rautio, J.; Kumpulainen, H.; Heimbach, T.; Oliyai, R.; Oh, D. et al. Prodrugs: design and clinical applications. *Nat. Rev. Drug Discov.* 2008, 7, 255, (c) T. Higuchi and V. Stella, *Prodrugs as Novel Delivery Systems* (1987) 14 of the A.C.S. Symposium Series, and in (d) *Bioreversible Carriers in Drug Design,* (1987) Edward B. Roche, ed., American Pharmaceutical Association and Pergamon Press. More specifically, compounds of Formula I (or any embodiment thereof and pharmaceutically acceptable salts thereof) are prodrug modifications of Compound A. The compounds of Formula I may be converted intracellularly (in vivo or in vitro) to the corresponding Compound A. The conversion may occur by one or more mechanisms, e.g., an enzyme-catalyzed chemical reaction, a metabolic chemical reaction, and/or a spontaneous chemical reaction (e.g., solvolysis), such as, for example, through hydrolysis in blood. While not wishing to be bound by any particular theory, Compound A is generally understood to be responsible for inhibiting PDE10.

Another embodiment of the present invention is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as, high performance liquid chromatography, and/or mass spectrometry or NMR techniques. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual stereoisomer.

The compounds of Formula I herein, and pharmaceutically acceptable salts thereof, are useful for inhibition of PDE10 in vitro and in vivo. "Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, may provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum may result in increased cAMP/cGMP signaling and striatal output, which has the potential to restore behavioral inhibition that is impaired in cognitive disease such as schizophrenia. Regulation and integration of glutamatergic and dopaminergic inputs may enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity. As used herein, the term "selective PDE10 inhibitor" refers to an organic molecule that effectively inhibits an enzyme from the PDE10 family to a greater extent than enzymes from the PDE 1-9 or PDE11 families. In one embodiment, a selective PDE10 inhibitor is an organic molecule having a Ki for inhibition of PDE 10 that is less than or about one-tenth that for a substance that is an inhibitor for another PDE enzyme.

Phosphodiesterase enzymes including PDE10 have been implicated in a wide range of biological functions. This has suggested a potential role for these enzymes in a variety of disease processes in humans or other species. The compounds of the present invention have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington DC) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR, and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and frontal temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive declirte, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy. Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE10 inhibitors may be readily determined without undue experimentation using a fluorescence polarization (FP) methodology that is well known in the art (Huang, W., et al., *J. Biomol Screen*, 2002, 7: 215). In particular, the compounds as disclosed herein had activity in reference assays by exhibiting the ability to inhibit the hydrolysis of the phosphate ester bond of a cyclic nucleotide. Any compound, for example Compound A, exhibiting a Ki (inhibitory constant) below 1 µM would be considered a PDE10 inhibitor as defined herein.

The compounds of the present invention are prodrugs of Compound A and are useful as an agent for example, in the in the inhibition of phosphodiesterase 10 (PDE10), for the treatment of central nervous system disorders associated with phosphodiesterase 10 (PDE10), to facilitate administration of Compound A and treatment of schizophrenia, including a variety neurological, psychotic, anxiety and/or movement disorders.

In a typical experiment the PDE10 inhibitory activity of compounds such as Compound A was determined in accordance with the following experimental method. PDE10A2 was amplified from human fetal brain cDNA (Clontech, Mountain View, CA) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, CA) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, CA) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, CA). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, CA (product #R8139). IMAP® technology has been applied previously to phosphodiesterase assays (Huang, W., et al., *J. Biomol Screen*, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. *Neuropharmacology* (2006) 51:386-396; Becker, et al. *Behav Brain Res* (2008) 186(2):155-60; Threlfell, et al., *J Pharmacol Exp Ther* (2009) 328(3):785-795), 2-{4-[pyridin-4-yl-1-(2,2,2-trifluoroethyl)-IH-pyrazol-3-yl]phenoxymethyl}quinoline succinic acid or 2-[4-(1-methyl-4-pyridin-4-yl-IH-pyrazol-3-yl)-phenoxymethyl]quinoline succinic acid (see Schmidt, et al. *Pharmacol Exp Ther* (2008) 325:681-690; Threlfell, et al., *J Pharmacol Exp Ther* (2009) 328(3): 785-795). 0% of inhibition is determined by using DMSO (1% final concentrations).

A Labcyte Echo 555 (Labcyte, Sunnyvale, CA) is used to dispense 200 nL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product #R7506), at a final concentration of 50 nM are made in the assay buffer (10 mM Tris HCl, pH 7.2, 10 mM MgCl$_2$, 0.05% NaN3 0.01% Tween-20, and 1 mM DTT). The enzyme and the substrate are then added to the assay plates in two consecutive additions of 10 µL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer EnVision™ plate reader (Waltham, MA).

Fluorescence polarization (mP) was calculated from the parallel (S) and perpendicular (P) fluorescence of each sample well and the analogous values for the median control well, containing only substrate (So and Po), using the following equation:

Polarization $(mP)=1000*(S/So-P/Po)/(S/So+P/Po)$.

Dose-inhibition profiles for each compound were characterized by fitting the mP data to a four-parameter equation given below. The apparent inhibition constant (KI), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., *JALA*, 2003, 8: 54-63, using the following equation:

$$mP = \frac{(0\% \ mP - 100\% \ mP)(Imas - Imin)}{1 + \frac{[[Drug]]^{nH}}{(10^{-pK_1}(1 + [Substrate]))}} +$$

$$100\% \ mP + (\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, CA): PDE1A (Cat #60010), PDE3A (Cat #60030), PDE4A1A (Cat #60040), PDE5A1 (Cat #60050), PDE6C (Cat #60060), PDE7A (Cat #60070), PDE8A1 (Cat #60080), PDE9A2 (Cat #60090), PDE11A4 (Cat #60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each often solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, CA) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, CA, product #R7506 or cGMP #R7508), at a final concentration of 50 nM were made in the assay buffer (10 mM Tris HCl, pH 7.2, 10 mM MgCh, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µLand then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent KM values for each enzyme and substrate combination:

PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

Compound A had activity in inhibiting the human PDE10 enzyme, generally with an Ki of less than about 1 µM. Such a result is indicative of the intrinsic activity of the compounds in use as inhibitors of the PDE10 enzyme. Data on pro drugs of Compound A is provided in the following Examples.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200.

Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRis), monoamine oxidase inhibitors (MAOis), reversible inhibitors of monoamine oxidase (RIMAs), serotonin and noradrenaline reuptake inhibitors (SNRis), corticotropin releasing factor (CRF) antagonists, a-adrenoreceptor antagonists, neurokinin-1 receptor antagonists, atypical anti-depressants, benzodiazepines, 5-HT1A agonists or antagonists, especially 5-HT$_1$A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, intracerebroventricular (ICV), intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography; DMSO: dimethyl sulfoxide; TFA: trifluoroacetic acid; aqu.: aqueous; CELITE: diatomaceous earth; acetonitrile; UPLC: ultra performance liquid chromatography, XRPD: x-ray powder diffraction, In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Several methods for preparing the compounds of this invention are described in the following Schemes and Examples

EXAMPLES

General Methods

Solvents, reagents, and intermediates that are commercially available were used as received. Reagents and intermediates that are not commercially available were prepared in the manner as described below. $^1$H NMR spectra are reported as ppm downfield from Me$_4$Si with number of protons, multiplicities, and coupling constants in Hertz indicated parenthetically. Where LC/MS data are presented, the observed parent ion is given. Flash column chromatography was performed using pre-packed normal phase silica or bulk silica, typically using a gradient elution of hexanes or petroleum ether and ethyl acetate, from 100% hexanes/petroleum ether to 100% ethyl acetate. Reverse-phase purification was performed using a Sunfire Prep C18 OBD 5 μm (30×150 mm) or 10 μm (50×150 mm) column, typically using a gradient elution of acetonitrile and water with 0.1% trifluoroacetic acid as a modifier.

Example 1

(5-Methyl-2-oxo-1,3-dioxol-4-yl)methyl ((5-methyl-1,3,4-thiadiazol-2-yl)methyl)(2-methyl-6-(((1S,2S)-2-(5-methylpyridin-2-yl)cyclopropyl)methoxy)pyrimidin-4-yl)carbamate

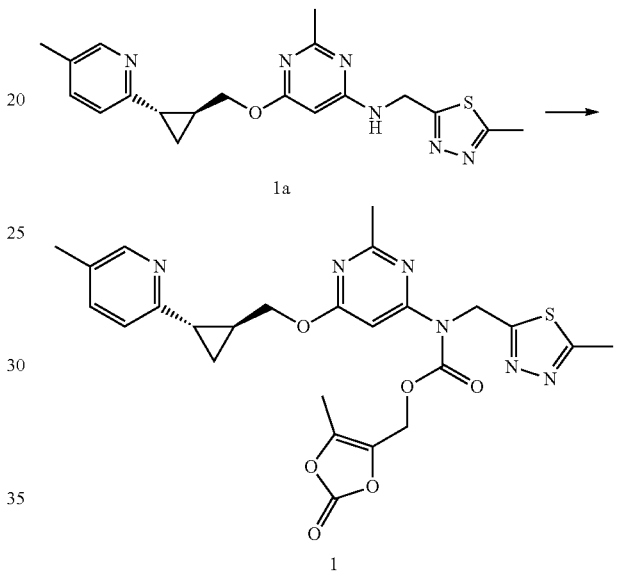

Step A—Synthesis of Compound 1

A solution of 2-methyl-N-((5-methyl-1,3,4-thiadiazol-2-yl)methyl)-6-(((1S,2S)-2-(5-methylpyridin-2-yl)cyclopropyl)methoxy)pyrimidin-4-amine (1a, 500 mg, 1.31 mmol) and (5-methyl-2-oxo-1,3-dioxol-4-yl)methyl 4-nitrophenyl carbonate [CAS 173604-87-0] (867 mg, 2.94 mmol) in DMF (6.5 mL) was treated with triethylamine (729 μL, 5.23 mmol) and then heated at 70° C. for 4.5 h. Additional (5-methyl-2-oxo-1,3-dioxol-4-yl)methyl 4-nitrophenyl carbonate (490 mg, 1.66 mmol) and triethylamine (600 μL, 4.30 mmol) were added and heating continued overnight. Additional (5-methyl-2-oxo-1,3-dioxol-4-yl)methyl 4-nitrophenyl carbonate (300 mg) and triethylamine (400 μL) were added and heating continued another 6.5 h. Additional (5-methyl-2-oxo-1,3-dioxol-4-yl)methyl 4-nitrophenyl carbonate (260 mg) was added and heating continued overnight again.

The cooled reaction was diluted with water and basified with saturated, aqu. Na$_2$CO$_3$, then extracted twice with ethyl acetate. The combined organics were washed with a combination of brine and saturated, aqu. Na$_2$CO$_3$, dried over MgSO$_4$, and concentrated. The residue was purified using preparative HPLC (reverse-phase C-18), eluting with acetonitrile/water+0.1% TFA 10-50%. Fractions containing the target compound were combined, basified with saturated, aqu. NaHCO$_3$, and extracted with ethyl acetate. The organics were washed with brine, dried over MgSO$_4$, and concentrated to give 1. MS: m/z 539.2=[M+H]. $^1$H NMR (600

MHz, CDCl₃, ppm): δ 8.27 (s, 1H), 7.36 (d, J=8.4 Hz, 1H), 7.14 (s, 1H), 7.05 (d, J=8.4 Hz, 1H), 5.58 (s, 2H), 4.98 (S, 2H), 4.40-4.42 (m, 1H), 4.31-4.34 (m, 1H), 2.73 (s, 3H), 2.54 (s, 3H), 2.28 (s, 3H), 2.20 (s, 3H), 2.05-2.09 (m, 1H), 1.87-1.92 (m, 1H), 1.29-1.33 (m, 1H), 1.04-1.07 (m, 1H).

Example 2

N-((5-Methyl-1,3,4-thiadiazol-2-yl)methyl)-N-(2-methyl-6-(((1S,2S)-2-(5-methylpyridin-2-yl)cyclopropyl)methoxy)pyrimidin-4-yl)-S-phenylthiohydroxylamine

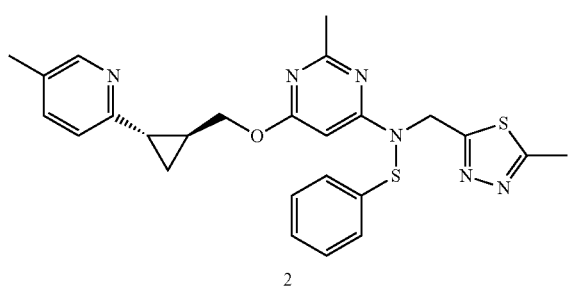

Step A—Synthesis of Compound 2

A solution of 1a (300 mg, 0.784 mmol) and N-(phenylthio)phthalimide (220 mg, 0.863 mmol) in DMF (6.5 mL) was stirred at 100° C. overnight. The cooled reaction was concentrated, and the residue was purified using preparative HPLC (reverse-phase C-18), eluting with acetonitrile/water+0.1% TFA 10-55%. Fractions containing the target were combined, basified with saturated, aqu. NaHCO₃, and extracted with ethyl acetate. The organics were washed with brine, dried over MgSO₄, and concentrated. The residue was purified a second time using preparative HPLC (reverse-phase C-18), eluting with acetonitrile/water+0.1% TFA 10-55%. Fractions containing the target compound were combined, basified with saturated, aqu. NaHCO₃, and extracted with ethyl acetate. The organics were washed with brine, dried over MgSO₄, and concentrated to give 2. MS: m/z 491.1=[M+H]. ¹H NMR (600 MHz, CDCl₃, ppm): δ 8.26 (s, 1H), 7.34 (d, J=7.2 Hz, 1H), 7.26-7.29 (m, 2H), 7.17-7.20 (m, 1H), 7.11 (d, J=8.4 Hz, 2H), 7.02 (d, J=7.8 Hz, 1H), 6.58 (s, 1H), 5.46 (s, 2H), 4.31-4.34 (m, 1H), 4.26-4.29 (m, 1H), 2.71 (s, 3H), 2.54 (s, 3H), 2.26 (s, 3H), 2.02-2.05 (m, 1H), 1.82-1.88 (m, 1H), 1.25-1.30 (m, 1H), 1.01-1.04 (m, 1H).

Example 3

N-((5-Methyl-1,3,4-thiadiazol-2-yl)methyl)-N-(2-methyl-6-(((1S,2S)-2-(5-methylpyridin-2-yl)cyclopropyl)methoxy)pyrimidin-4-yl)benzamide

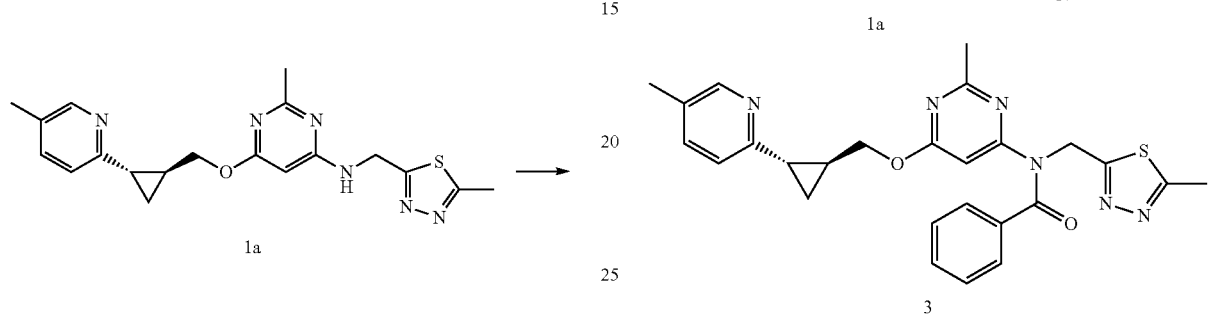

Step A—Synthesis of Compound 3

A solution of 1a (250 mg, 0.654 mmol) in dioxane (2.61 mL) was treated with diisopropylethylamine (171 µL, 0.980 mmol) and benzoyl chloride (99 µL, 0.85 mmol) and stirred at room temperature. After 3.5 h, additional diisopropylethylamine (57 µL and benzoyl chloride (38 µL) were added and stirring continued overnight. The reaction was diluted with brine and saturated, aqu. NaHCO₃, then extracted with ethyl acetate, washed with brine, dried over MgSO₄, and concentrated. The residue was purified using preparative HPLC (reverse-phase C-18), eluting with acetonitrile/water+0.1% TFA 10-45%. Fractions containing the target were combined, basified with saturated, aqu. NaHCO₃, and extracted with ethyl acetate. The organics were washed with brine, dried over MgSO₄, and concentrated to give 3. MS: m/z 487.2=[M+H]. ¹H NMR (600 MHz, CDCl₃, ppm): δ 8.25 (s, 1H), 7.39-7.44 (m, 3H), 7.33-7.35 (m, 1H), 7.30 (t, J=7.8 Hz, 2H), 6.99 (d, J=7.8 Hz, 1H), 5.92 (s, 1H), 5.61 (s, 2H), 4.18-4.25 (m, 2H), 2.73 (s, 3H), 2.50 (s, 3H), 2.27 (s, 3H), 1.94-1.97 (m, 1H), 1.74-1.80 (m, 1H), 1.22-1.26 (m, 1H), 0.93-0.96 (m, 1H).

Example 4

Pentyl ((5-methyl-1,3,4-thiadiazol-2-yl)methyl)(2-methyl-6-(((1S,2S)-2-(5-methylpyridin-2-yl)cyclopropyl)methoxy)pyrimidin-4-yl)carbamate

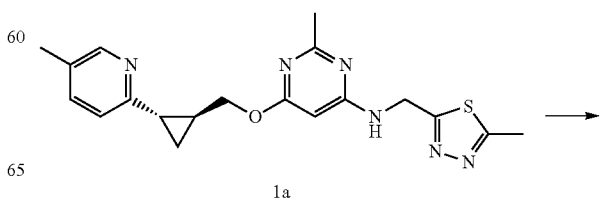

27
-continued

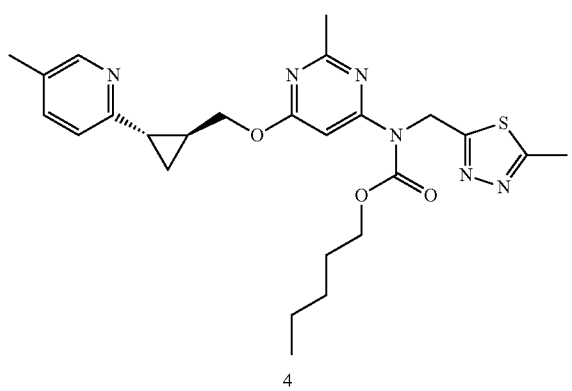

4

Step A—Synthesis of Compound 4

A solution of 1a (150 mg, 0.392 mmol) in DMF (1.12 mL) was treated with 4-dimethylaminopyridine (9.6 mg, 0.078 mmol), triethylamine (131 μL, 0.941 mmol), and pentyl chloroformate (227 μL, 1.57 mmol) and then heated at 60° C. for 4.5 h. Additional pentyl chloroformate (114 μL) was added and heating continued overnight. Additional triethylamine (131 μL) and pentyl chloroformate (227 μL) were added the following morning and again in the afternoon, and heating continued overnight. The following morning more triethylamine (131 μL) and pentyl chloroformate (227 μL) were added the following morning and again in the afternoon, and heating continued overnight.

The cooled reaction was diluted with water and basified with saturated, aqu. NaHCO$_3$, then extracted twice with ethyl acetate. The combined organics were washed with a combination of brine and saturated, aqu. Na$_2$CO$_3$, dried over MgSO$_4$, and concentrated. The residue was purified by silica gel chromatography eluting with 0-65% EtOAc/hexanes to give 4. MS: m/z 497.3=[M+H]. $^1$H NMR (600 MHz, CDCl$_3$, ppm): δ 8.27 (s, 1H), 7.35 (dd, J=8.4, 1.8 Hz, 1H), 7.21 (s, 1H), 7.04 (d, J=8.4 Hz, 1H), 5.58 (s, 2H), 4.37-4.40 (m, 1H), 4.30-4.33 (m, 1H), 4.21 (t, J=6.6 Hz, 2H), 2.72 (s, 3H), 2.53 (s, 3H), 2.27 (s, 3H), 2.04-2.07 (m, 1H), 1.86-1.89 (m, 1H), 1.65-1.69 (m, 2H), 1.25-1.33 (m, 5H), 1.03-1.06 (m, 1H), 0.88 (t, J=6.6 Hz, 3H).

Example 5

(((((5-Methyl-1,3,4-thiadiazol-2-yl)methyl)(2-methyl-6-(((1S,2S)-2-(5-methylpyridin-2-yl)cyclopropyl)methoxy)pyrimidin-4-yl)carbamoyl)oxy)methyl benzoate

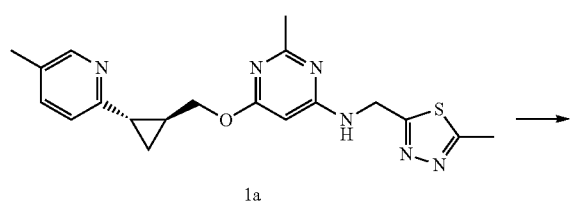

1a

28
-continued

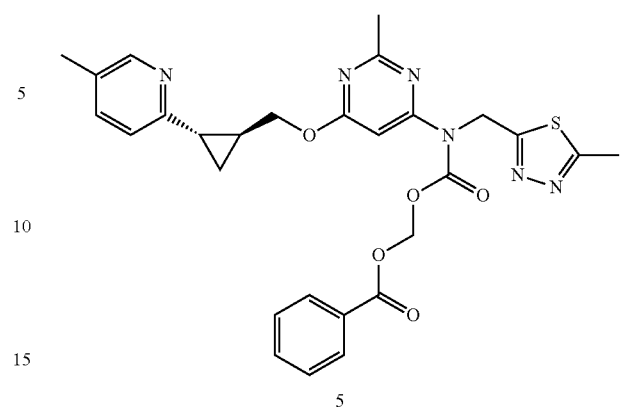

5

Step A—Synthesis of Compound 5

A solution of 1a (150 mg, 0.392 mmol) in dichloromethane (980 μL) was cooled at 0° C. and treated with chloromethyl chloroformate (105 μL, 1.18 mmol) quickly dropwise, then allowed to warm to room temperature. After 2 h, the reaction was diluted with dichloromethane and saturated, aqu. NaHCO$_3$. The organics were separated and the aqueous phase was extracted a second time with dichloromethane. The combined organics were washed with brine, dried over MgSO$_4$, and concentrated. The residue was taken up in DMF (2 mL) and benzoic acid (144 mg, 1.18 mmol) and cesium carbonate (192 mg, 0.588 mmol) were added and the reaction was heated at 70° C. for 3 h. The cooled reaction was purified using preparative HPLC (reverse-phase C-18), eluting with acetonitrile/water+0.1% TFA 10-70%. Fractions containing the target were combined, basified with saturated, aqu. NaHCO$_3$, and extracted with ethyl acetate. The organics were washed with brine, dried over MgSO$_4$, and concentrated to give 5. MS: m/z 561.3=[M+H]. $^1$H NMR (600 MHz, CDCl$_3$, ppm): δ 8.27 (s, 1H), 8.04 (d, J=7.2 Hz, 2H), 7.60 (t, J=6.6 Hz, 1H), 7.45 (t, J=7.8 Hz, 2H), 7.36 (d, J=6.6 Hz, 1H), 7.19 (s, 1H), 7.05 (d, J=7.8 Hz, 1H), 6.11 (s, 2H), 5.61 (s, 2H), 4.37-4.40 (m, 1H), 4.30-4.33 (m, 1H), 2.60 (s, 3H), 2.52 (s, 3H), 2.28 (s, 3H), 2.05-2.08 (m, 1H), 1.85-1.91 (m, 1H), 1.29-1.32 (m, 1H), 1.03-1.06 (m, 1H).

Example 6

Alternative Preparation of Compound 5

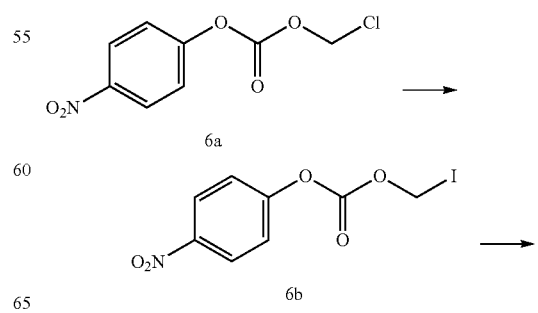

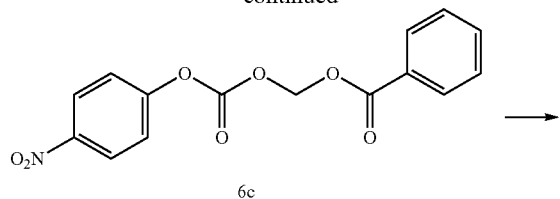

6c

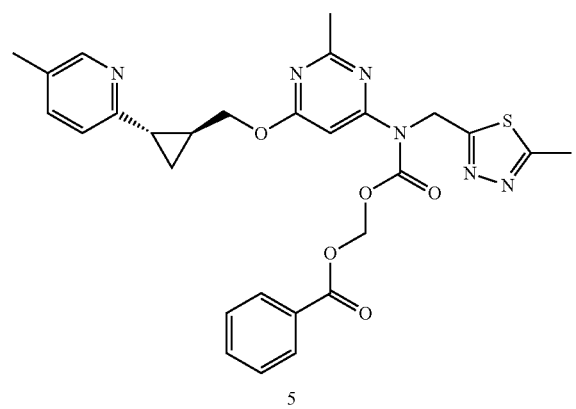

5

Step A—Synthesis of Compound 6b

A solution of 6a (5.00 g, 21.6 mmol) in acetone (54.0 mL) was treated with sodium iodide (9.71 g, 64.8 mmol) and sodium bicarbonate (0.363 g, 4.32 mmol), and the resulting suspension was heated at 40° C. for 12 h. Additional 6a (5.00 g, 21.6 mmol), sodium iodide (9.71 g, 64.8 mmol), sodium bicarbonate (0.363 g, 4.32 mmol), and acetone (25 mL) were added, and heating continued overnight. The cooled reaction was diluted with acetone and filtered through Celite™, washing with acetone. The yellow filtrate was concentrated and the resulting solids were taken up in water and extracted three times with ethyl acetate. The combined organics were washed with saturated, aqu. $Na_2SO_3$ solution, then washed with brine, dried over $MgSO_4$, and concentrated to give 6b as an oil which was used without further purification. $^1$H NMR (600 MHz, $CDCl_3$, ppm): δ 8.30-8.32 (m, 2H), 7.42-7.44 (m, 2H), 6.07 (s, 2H).

Step B—Synthesis of Compound 6c

A mixture of 6b (13.2 g, 40.9 mmol), benzoic acid (7.49 g, 61.3 mmol), and silver carbonate (16.90 g, 61.3 mmol) in toluene (272 mL) was heated at 80° C. for 4 h and 15 mins. The cooled reaction was filtered through Celite™, washing with toluene. The filtrate was washed with water, then with brine, dried over $MgSO_4$, and concentrated. The residue was purified by silica gel chromatography eluting with 0-30% EtOAc/hexanes to give 6c an oil. $^1$H NMR (600 MHz, $CDCl_3$, ppm): δ 8.28-8.31 (m, 2H), 8.11-8.13 (m, 2H), 7.63-7.66 (m, 1H), 7.48-7.51 (m, 2H), 7.41-7.44 (m, 2H), 6.14 (s, 2H).

Step C—Synthesis of Compound 5

A mixture of 1a (100 mg, 0.261 mmol) and 6c (190 mg, 0.588 mmol) in dichloroethane (800 μL) and cyclohexane (800 μL) were added and heated at 85° C. overnight. The cooled reaction was diluted with dichloromethane and washed with half-saturated, aqu. $Na_2CO_3$. The organics were separated and the aqueous portion was extracted three times with dichloromethane. The combined organics were washed with half-saturated, aqu. $Na_2CO_3$, dried over $MgSO_4$, and concentrated. The residue was purified by silica gel chromatography eluting with 10-100% EtOAc/hexanes. The isolated material was purified a second time by silica gel chromatography eluting with 10-100% EtOAc/hexanes to give 5.

The following compounds of the present invention were made using methodology described in Examples 5 or 6 above, substituting the appropriate reactants and/or reagents:

| Compd | Structure | Name | MS [M + H] |
|---|---|---|---|
| 6 | 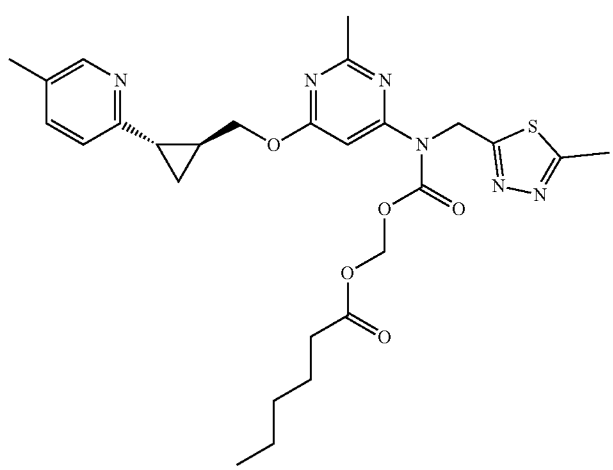 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl hexanoate | 555.3 |

| Compd | Structure | Name | MS [M + H] |
|---|---|---|---|
| 7 | 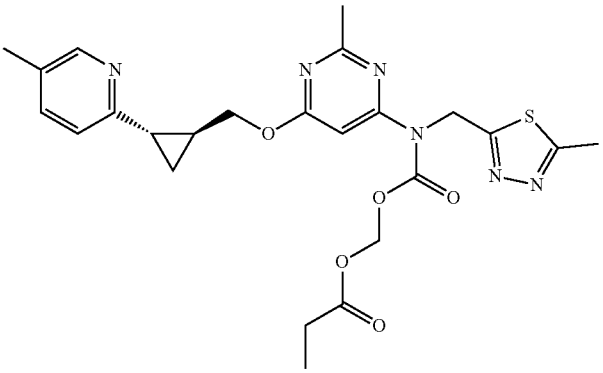 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl propanoate | 513.3 |
| 8 | 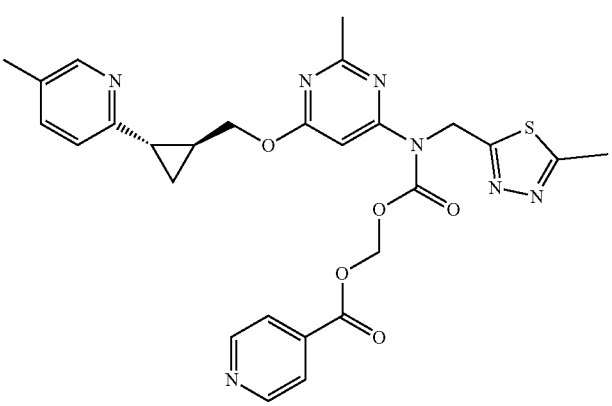 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl pyridine-4-carboxylate | 562.4 |
| 9 | 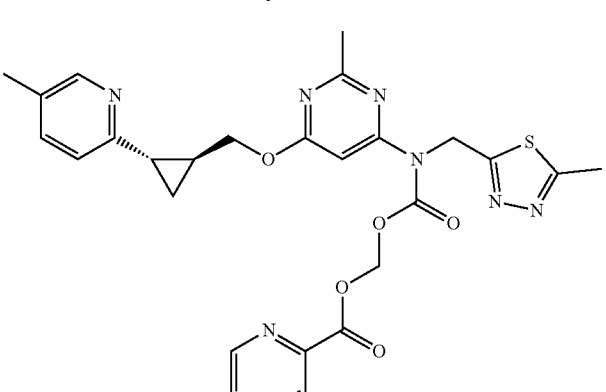 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl pyridine-2-carboxylate | 562.4 |
| 10 | 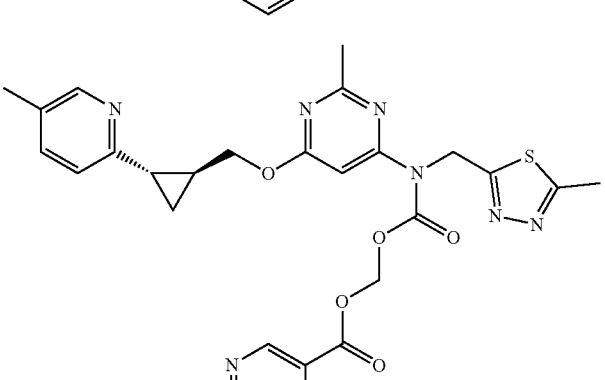 | ({(2-Methyl-6-{[(1S,2S)-2-(5-methylpyridin-2-ylcyclopropyl]methoxy}pyrimidin-4-yl)|(5-methyl-1,3,4-thiadiadol-2-yl)methyl]carbamoyl}oxy)methyl pyridine-3-carboxylate | 562.5 |

-continued

| Compd | Structure | Name | MS [M + H] |
|---|---|---|---|
| 11 | 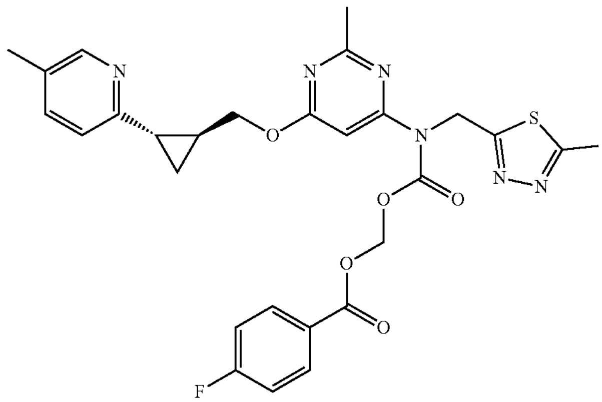 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 4-fluorobenzoate | 579.5 |
| 12 | 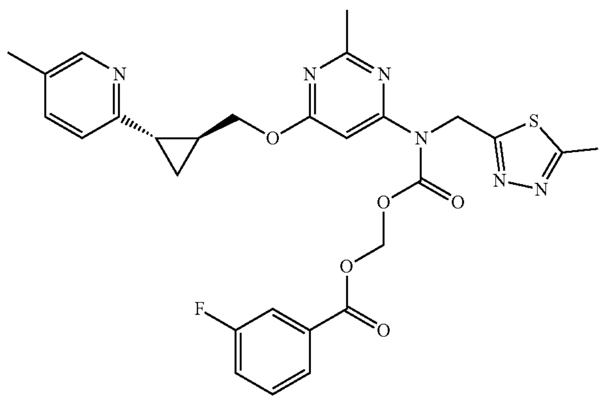 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 4-fluorobenzoate | 579.5 |
| 13 | 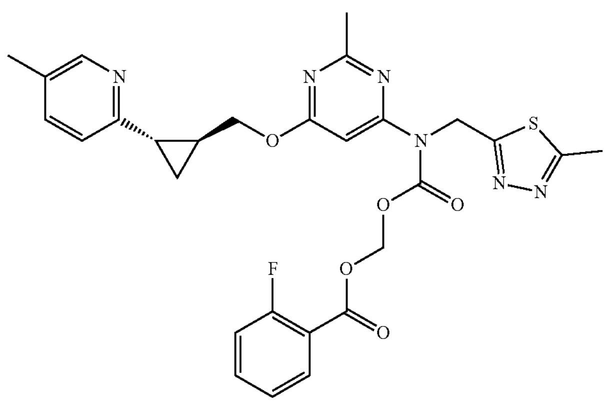 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 2-fluorobenzoate | 579.5 |
| 14 | 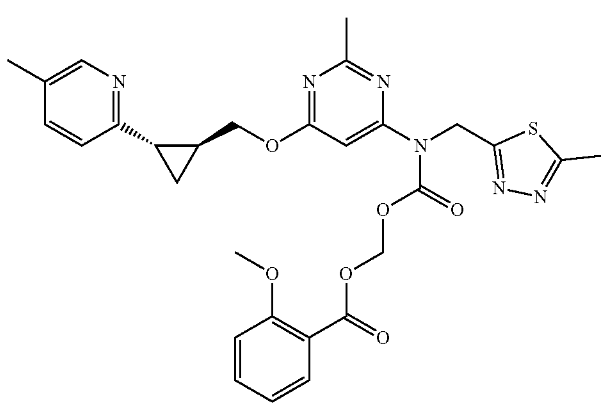 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 2-methoxybenzoate | 591.5 |

-continued

| Compd | Structure | Name | MS [M + H] |
|---|---|---|---|
| 15 | 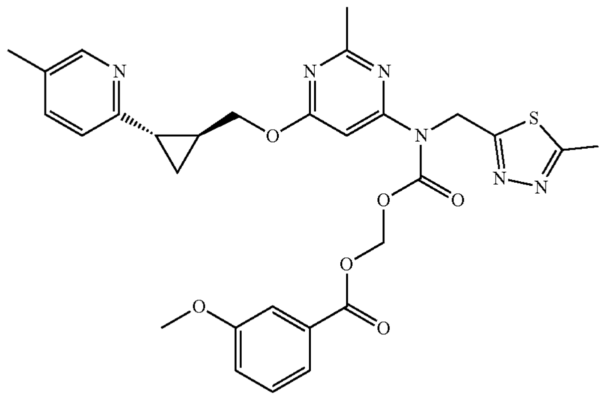 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 3-methoxybenzoate | 591.5 |
| 16 | 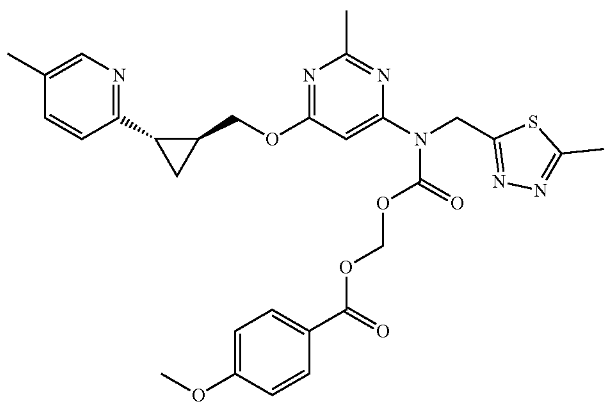 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 4-methoxybenzoate | 591.5 |
| 17 | 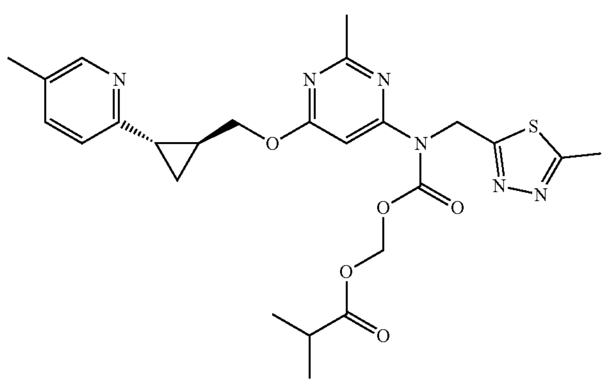 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 2-methoxypropanoate | 527.5 |
| 18 | 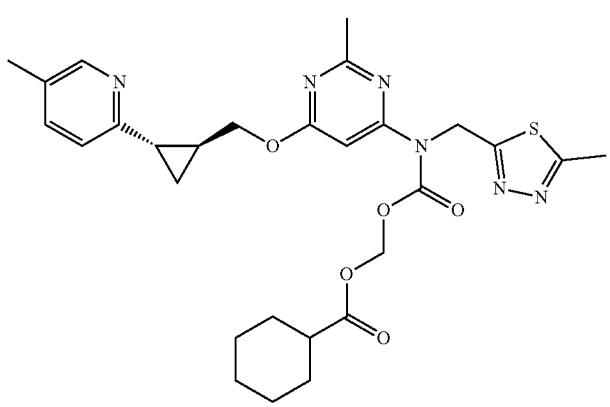 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl cyclohexanecarboxylate | 567.5 |

| Compd | Structure | Name | MS [M + H] |
|---|---|---|---|
| 19 | 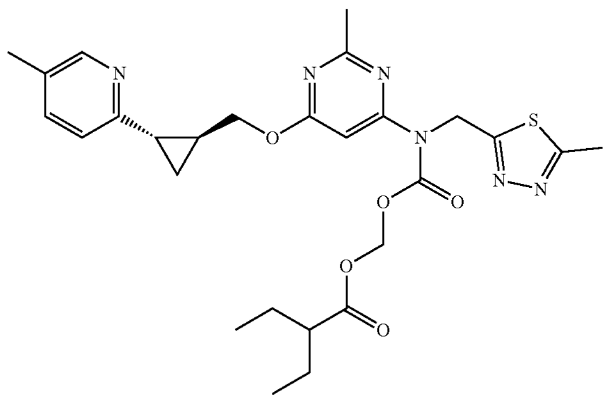 | ({(2-Methyl-6-{[(1S,2S)-2-(5-methylpyridin-2-yl)cyclopropyl]methoxy}pyrimidin-4-yl)[(5-methyl-1,3,4-thiadiazol-2-yl)methyl]carbamoyl}oxy)methyl 2-ethylbutanoate | 555.5 |

Solubility and Stability

Aqueous solubility of the compounds was measured by suspending, sonicating (30 minutes), and slurrying (2 hours, 1000 rpm) excess solid (typically 5-10 mg) in phosphate buffered saline at pH 7, or equivalent pH 7 buffer. The suspension was then sonicated again for 30 minutes and stirred again at 1000 rpm for at least 6-24 hours. Approximately 400 µL of sample was removed and placed into spin filters. Each sample was spun at 14K rpm for 10 minutes using a 0.45 µm PVDF spin filter. A portion of the filtrate was removed and diluted with 1:1 ACN:H$_2$O. The resultant samples were analyzed using UPLC analysis. Retains of the solids were checked by XRPD to determine if the material was crystalline or amorphous. Solubility of Compound A was measured at 140 µg/mL at pH 7.4 in PBS buffer solution. Compounds 1 through 19 as disclosed in Table 1 exhibited lower aqueous solubility thus allowing for controlled release over extended periods Solubility of Compound A was measured at 140 µg/mL at pH 7.4 in PBS buffer solution. Compounds 1 through 19 as disclosed in Table 1 exhibited lower aqueous solubility thus allowing for controlled release over extended periods for example over a period of days or weeks.

Plasma stability of the compounds 1-19 (1 µM) was evaluated in frozen monkey and human plasma at 37° C. in a 10% CO$_2$ environment. The stability of the analyte was assessed by determining the percentage of drug loss over the course of 0, 0.25, 0.5, 1, and 3 hr. In addition, the appearance of Compound A was determined for the same time course. Percent of drug loss as based on ratio with internal standard. Analyte concentrations were measured by LC/MS/MS. Linear regression was performed with log transformed percent of average TO values and linear time values. The elimination rate constant (ke) was calculated from the slope of this regression line and the half-life (T$_{1/2}$) calculated based on the elimination rate constant.

TABLE 1

| Compound | Aqu. Solubility µg/mL$^a$ | T$_{1/2}$ Human Plasma (hours) | T$_{1/2}$ Monkey Plasma (hours) |
|---|---|---|---|
| 1 | 2.3 | 0.06 | 0.11 |
| 2 | BLQ | 0.29 | 0.08 |
| 3 | 19 | 3.03 | 1.15 |
| 4 | 0.008 | 6.86 | 1.73 |
| 5 | 0.02 | 1.74 | 1.31 |
| 6 | 0.02 | 0.35 | 0.24 |
| 7 | 15 | 0.08 | 0.09 |
| 8 | 0.139 | 0.19 | 0.16 |
| 9 | 0.058 | 0.12 | 0.10 |
| 10 | 0.050 | 0.93 | 0.51 |
| 11 | 0.07 | 1.08 | 0.72 |
| 12 | 0.18 | 1.32 | 0.59 |
| 13 | 0.08 | 0.45 | 0.28 |
| 14 | 0.02 | 2.10 | 0.90 |
| 15 | 0.12 | 3.30 | 1.12 |
| 16 | 0.16 | 3.78 | 1.67 |
| 17 | 0.16 | 0.13 | 0.12 |
| 18 | 0.07 | 0.35 | 0.28 |
| 19 | 0.03 | 2.47 | 0.59 | a = µg/mL in pH 7.0 phosphate buffer for amorphous material
BLQ = below the limit of quantitation

What is claimed is:

1. A compound of structural Formula I:

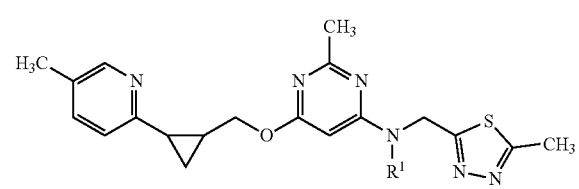

I or pharmaceutically acceptable salt thereof, wherein:
R$^1$ is —C(O)OC$_{1-6}$ alkyl, said alkyl optionally substituted with 1 to 3 groups of R$^a$, wherein the C$_{1-6}$ alkyl of —C(O)OC$_{1-6}$ alkyl is not t-butyl;
and
R$^a$ is independently selected from the group consisting of C$_{1-6}$ alkyl, OC$_{1-6}$ alkyl, oxo, and halogen.

2. A pharmaceutical composition which comprises a pharmaceutically acceptable carrier and a compound of claim 1, or a pharmaceutically acceptable salt thereof.

3. A method for treating schizophrenia, Parkinson's disease, Huntington's disease, obsessive-compulsive disorders, addiction or psychosis in a mammalian patient in need thereof which comprises administering to the patient a therapeutically effective amount of a compound of claim 1 or a pharmaceutically acceptable salt thereof.

\* \* \* \* \*